(12) United States Patent
Agudelo Otalora et al.

(10) Patent No.: US 12,137,876 B2
(45) Date of Patent: Nov. 12, 2024

(54) ENDOSCOPE ATTACHMENT ACCESSORY WITH TELEMETRIC FUNCTION FOR MEASURING DISTANCES AND SIZES ON INTERNAL SURFACES OF THE HUMAN BODY

(71) Applicant: UNIVERSIDAD DE LA SABANA, Chia (CO)

(72) Inventors: Luis Mauricio Agudelo Otalora, Bogota D.C. (CO); Mario Ricardo Arbulu Saavedra, Huila (CO); Luis Fernando Giraldo Cadavid, Huila (CO); William Daniel Moscoso Barrera, Bogota D.C. (CO)

(73) Assignee: UNIVERSIDAD DE LA SABANA, Chia (CO)

( * ) Notice: Subject to any disclaimer, the term of this patent is extended or adjusted under 35 U.S.C. 154(b) by 0 days.

(21) Appl. No.: 17/540,892

(22) Filed: Dec. 2, 2021

(65) Prior Publication Data
US 2022/0192472 A1    Jun. 23, 2022

(30) Foreign Application Priority Data
Dec. 21, 2020    (CO) ........................ NC2020/0016040

(51) Int. Cl.
*A61B 1/00*    (2006.01)
*A61B 1/06*    (2006.01)
*A61C 9/00*    (2006.01)

(52) U.S. Cl.
CPC ...... *A61B 1/00131* (2013.01); *A61B 1/00009* (2013.01); *A61B 1/00039* (2013.01); *A61B 1/0008* (2013.01); *A61B 1/00101* (2013.01); *A61B 1/063* (2013.01); *A61C 9/0046* (2013.01); *A61C 9/0053* (2013.01); *A61C 9/006* (2013.01)

(58) Field of Classification Search
CPC ............ A61B 1/00131; A61B 1/00009; A61B 1/00039; A61B 1/063; A61B 1/0605; A61B 1/0655; A61B 1/0661; A61B 1/0669; A61B 1/0684; A61B 1/00117; A61B 1/00126; A61B 1/07; A61B 1/00165; A61B 1/0008; A61B 1/00101; A61B 34/10; A61B 34/20; A61B 34/30; A61C 9/0046; A61C 9/0053; A61C 9/006
See application file for complete search history.

(56) References Cited

U.S. PATENT DOCUMENTS

| | | | |
|---|---|---|---|
| 8,780,362 B2 * | 7/2014 | Sharonov | G01B 11/14 356/625 |
| 9,113,822 B2 * | 8/2015 | Sharonov | A61B 1/00131 |
| 9,157,732 B2 * | 10/2015 | Sharonov | G01B 11/14 |
| 11,033,182 B2 * | 6/2021 | Hansen | A61B 90/30 |
| 12,075,981 B2 * | 9/2024 | Hansen | A61B 1/3132 |

(Continued)

*Primary Examiner* — Ryan N Henderson
(74) *Attorney, Agent, or Firm* — LUCAS & MERCANTI, LLP

(57) ABSTRACT

A biomedical device, an endoscope attachment accessory with telemetric function that allows to make measurements in internal surfaces of the body; the endoscope attachment accessory with telemetric function for measuring distances and sizes on internal surfaces of the human body comprising three modules, an image signal processing module for calculating distances, areas and volumes, a laser control module and an alignment module, all contained in a single housing.

5 Claims, 5 Drawing Sheets

(56) References Cited

U.S. PATENT DOCUMENTS

| | | | | |
|---|---|---|---|---|
| 2012/0040305 A1* | 2/2012 | Karazivan | A61B 1/00087 | 433/29 |
| 2012/0293812 A1* | 11/2012 | Sharonov | G01B 11/02 | 356/625 |
| 2013/0110005 A1* | 5/2013 | Sharonov | G01B 11/2513 | 600/587 |
| 2014/0188096 A1* | 7/2014 | Chia | G02B 6/3812 | 606/16 |
| 2018/0185093 A1* | 7/2018 | Misra | A61B 1/00098 | |
| 2018/0188080 A1* | 7/2018 | Waisman | A61B 18/24 | |
| 2019/0080454 A1* | 3/2019 | Hameed | A61B 1/00177 | |
| 2020/0015892 A1* | 1/2020 | Kim | A61B 18/1206 | |
| 2021/0038062 A1* | 2/2021 | Talbot | A61B 1/018 | |
| 2021/0038306 A1* | 2/2021 | McLoughlin | A61B 5/0075 | |
| 2021/0038310 A1* | 2/2021 | Bukesov | A61B 1/07 | |
| 2021/0038311 A1* | 2/2021 | Shelton | A61B 5/4836 | |
| 2021/0128238 A1* | 5/2021 | Chabok | A61N 5/0622 | |
| 2021/0282856 A1* | 9/2021 | Kim | A61B 18/22 | |
| 2022/0226063 A1* | 7/2022 | Leão | A61B 90/35 | |

* cited by examiner

ENDOSCOPE ATTACHMENT ACCESSORY WITH TELEMETRIC FUNCTION FOR MEASURING DISTANCES AND SIZES ON INTERNAL SURFACES OF THE HUMAN BODY

CROSS REFERENCE TO RELATED APPLICATION

This Application claims priority of Colombian Patent Application No. NC2020/0016040 filed Dec. 21, 2020 the contents of which is incorporated herein by reference.

FIELD OF THE INVENTION

The present invention relates to the Biomedical engineering sector, specifically to the development of devices with application in the field of medicine.

The present invention corresponds to the development of an accessory for attachment to an endoscope with telemetric function for measuring distances and sizes on internal surfaces of the human body, wherein said accessory allows distance and/or area measurements on internal surfaces of the body, and mainly comprises an alignment module, a laser control module and a processing module, integrated in a single unit. In particular, the three modules are housed in an external housing.

BACKGROUND OF THE INVENTION

According to the World Health Organization (WHO), surgical interventions are responsible for 13% of disability-adjusted life years—a measure of years lost due to disease or its treatment. The WHO reports mortality rates as high as 5%, and complications in up to 25% of surgeries.

Thus, the development of safer and more effective surgical devices and techniques is therefore an issue in the technique, where devices that allow to perform more precise surgeries are a priority. This need has been met by the development of minimally invasive surgeries such as laparoscopic surgery and robotic surgery. The measurement of certain distances and internal structures during laparoscopic surgery is useful to define pathology, or to determine the dimensions of prostheses or other implantable devices. This measurement of distances is usually done based on the observer's naked eye and subjective estimation with methods that are limited in precision and accuracy.

In view of the above, it has given way to developments such as that disclosed in utility model CN201569427 which provides a device for measuring the size of an object, but does not include systems or mechanisms for aligning devices and measuring distances. The laser telemeter of this invention comprises a measuring scale, a sliding block movable on said scale, and a first laser generator disposed on the sliding block, and a second laser generator fixed at the reference position. The block can move on the scale and drive the first laser from the reference position to a second point. This telemeter allows to accurately measure the distance between two points through a viewing hole and eliminate errors caused by naked eye estimation, improving the reliability and accuracy of distance estimations. However, the telemeter of this invention is not designed for use in laparoscopic surgeries, and because of its dimensions and the fact that it includes two laser generators, it cannot be used in conjunction with a fiberscope.

On the other hand, U.S. Pat. No. 5,434,669 refers to an interferometric measuring endoscope for accurately determining the location of internal diseases within organs of human bodies. The accessory comprises: a source of laser radiation and includes a device for producing interference fringes; a device for projecting the interference fringes onto a surface of an object to be measured; a device for scanning the interference fringes; an imaging device for reading brightness vibrations on the surface of the object to be measured that are caused by scanning the interference fringes; and a processing device capable of determining depths of concavities and heights of convexities on the surface of the measured object by calculating the data outputted from the imaging device. The development disclosed in the patent does not include a mechanism for alignment with the structures to be measured, nor means for analyzing the captured data.

U.S. Pat. No. 6,134,003 describes an endoscopic measurement system. Such a system comprises an optical radiation source, a reference reflector, a first optical guide leading to the reference reflector, and a second optical guide attached to the endoscopy unit. The system is to be used with an endoscopic unit in an elongated container, an optical fiber that is capable of rotating along said container, and an optical system. By means of a splitter and a detector, the device separates and captures the radiation emitted by the source and reflected in the reflector. Finally, a processor analyzes the data and generates an image of the structure, which has been scanned rotationally and longitudinally. Although the development allows the generation of high resolution images, it implies the use of endoscopic equipment with very specific characteristics, and its use in all types of laparoscopic surgeries is limited.

Similarly, the study published by Eric J. Seibel et al, entitled *Scanning Single Fiber Endoscopy: A new platform technology for integrated laser imaging, diagnosis, and future therapies*, describes an endoscopic fiber scanning device, and an ultra-thin, flexible endoscope that resembles a catheter in shape and size. In this study, a new type of endoscopic imaging has been developed and applied. The technology is based on a single optical fiber that is scanned at the distal tip of an ultrathin, flexible shaft that projects red, green, and blue laser light onto tissue in a spiral pattern. The resulting images are high quality, high resolution, color video. The device scans the red, green and blue laser light that is focused on the tissue. The backscattered light is collected by several optical fibers and the image is generated by a computer, one pixel at a time. The distal tip of the probe consists of a single mode cantilevered optical fiber, a piezo-electric tube actuator at the base of this cantilever, and focusing lenses distal to the tip of the cantilevered optical fiber. The scanned illumination light is collected by multi-mode optical fibers surrounding the fiber scanner and lens assembly.

The devices described in U.S. Pat. No. 5,434,669, 6,134,003A and in the study by Seibel and collaborators mentioned above, work on the basis of interferometry. These devices, by means of the interference of light waves, measure wavelengths of reflected light, concavities and convexities of internal organs and allow scanning of elements. Additionally, Sabiel's study uses three different types of lasers. The complexity of the elements that compose them and the way they work are very useful for scanning and imaging, but they are unnecessary if the main objective is to measure distances within the organs observable by a fiberscope. The above objective can be achieved with good precision and accuracy by attachment a single fiber laser to a fiberscope, which allows measurements to be made based on the principle of triangulation by computer analysis of endoscopic images.

The device disclosed in patent US2015/0305610 A1 includes a system for measuring surface areas of a tissue, wherein by transmitting optical signals via optical fiber, processing and calculation is performed. The system employs lasers and optical sensors to determine the distance. However, the attachment of the measuring elements to the endoscope is done manually by the users, which can generate variability between different observers. A precise automated attachment and alignment system for these elements such as that which is the subject of the present invention helps to control the variability in the attachment and alignment of the elements improving the precision and accuracy of the measurements made.

Despite the efforts made in the prior art in relation to this type of devices as previously mentioned, in the state of the art there is still a problem and a need related to the proper measurement of internal variables of the body through the use of other widely known medical devices, where it is highly necessary and desirable that such measurement is carried out by means of a device that can be attached easily and universally, without requiring specific external attachments, which raise the cost of operation and manufacture, while it can be used in a simple way by the health practitioner.

SUMMARY

The present invention provides a solution to the technical problem described above, since it refers to an endoscope attachment accessory with telemetric, alignment and automatic attachment function, comprising in a general, non-limiting way, three modules in a single unit (FIG. 1), wherein said accessory is attached to an endoscopic system and performs distance and/or area measurements on internal surfaces of the body.

In the general aspect of the invention, the endoscope attachment accessory with telemetric function of the invention comprises an alignment module, a laser control module and a signal processing module, which are integrated into a single unit. In particular, the three modules are housed in an external housing as illustrated in FIG. 1.

In one aspect of the invention, the endoscope attachment accessory with telemetric function comprises an alignment module (FIG. 2) comprising an electromechanical system that automatically and accurately aligns a laser fiber with the tip of an endoscope.

In the same aspect of the invention, the endoscope attachment accessory with telemetric function comprises a laser control module (FIG. 3) comprising an electronic system which generates a laser light beam which is reflected on the internal surfaces of the body and thus allows the distance and/or area to be calculated by means of the triangulation principle. In the same aspect, the endoscope attachment accessory with telemetric function comprises a signal processing module (FIG. 4) comprising processing means, which performs the analysis of images and/or videos coming from the camera of an endoscope. This computerized analysis of the endoscopic images and the projection site of the laser site, using the triangulation principle, calculates distances and areas.

BRIEF DESCRIPTION OF THE FIGURES

The present invention is more clearly understood from the following figures showing the components associated with the present system or apparatus, as well as the novel elements with respect to the state of the art, wherein, the figures are not intended to limit the scope of the invention, which is solely defined by the appended claims, wherein:

DETAILED DESCRIPTION OF THE INVENTION

Figure 1:
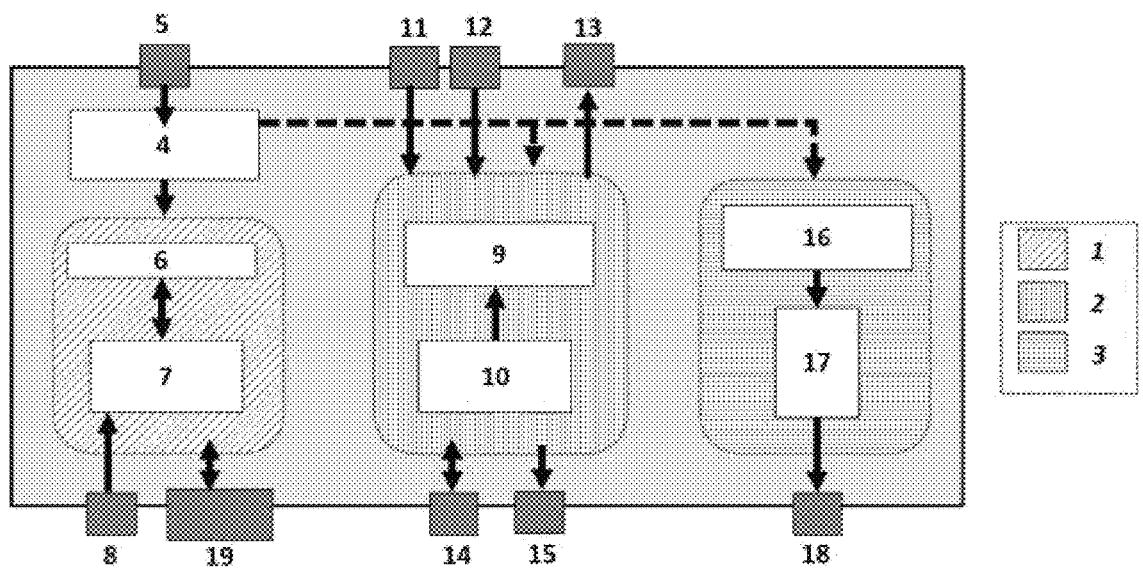
FIG. 1. Diagram of modules comprising the endoscope attachment accessory with telemetry function where the reference numbers indicated therein are defined as: (1) is the alignment module, (2) signal processing module comprising a microcontroller with analog and digital inputs and outputs, (3) laser control module, (4) power supply consisting of a 110/220 V AC source, (5) AC current input comprising an (6) aligner control electronic board, (7) coiler, (8) aligner input, (9) computer, (10) video converter, (11) keyboard input, (12) mouse input, (13) monitor output, (14) video input and output, (15) data output, (16) laser power control electronic means, (17) laser generator, (18) external fiber optic connector, (19) touch screen.
Figure 2:
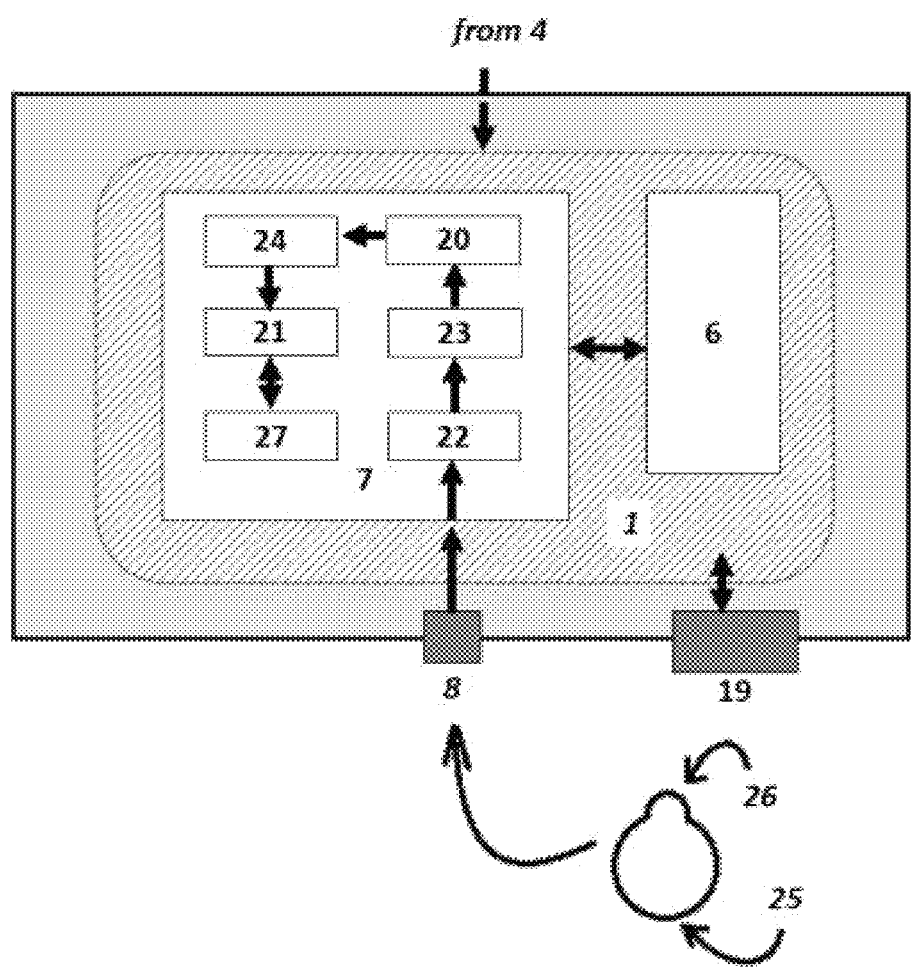
FIG. 2. Diagram of the alignment module forming part of the accessory of the present invention, wherein the reference numbers indicated therein are defined as: (1) the alignment module, (4) power supply, (6) electronic aligner control board, (7) coiler, (8) aligner input, (19) touch screen, (20) clamping medium coiler, (21) cutting mechanism, (22) alignment press, (23) gear and electronic control mechanism, (24) clamping medium meter with warning system, (25) endoscope input, (26) fiber optic input, (27) camera and sensor.
Figure 3:
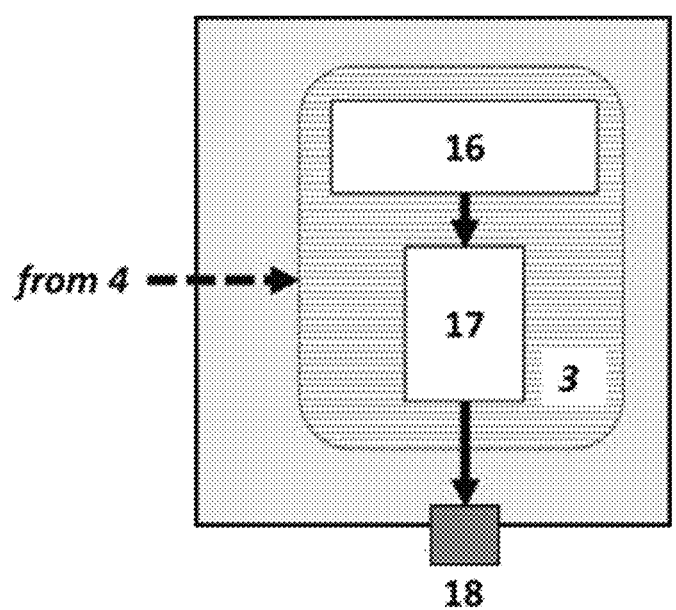
FIG. 3. Diagram of the laser control module forming part of the accessory of the present invention, wherein the reference numbers indicated therein are defined as: (3) laser control module, (4) power supply, (16) laser power control electronic means, (17) laser generator, (18) external fiber optic connector.
Figure 4:
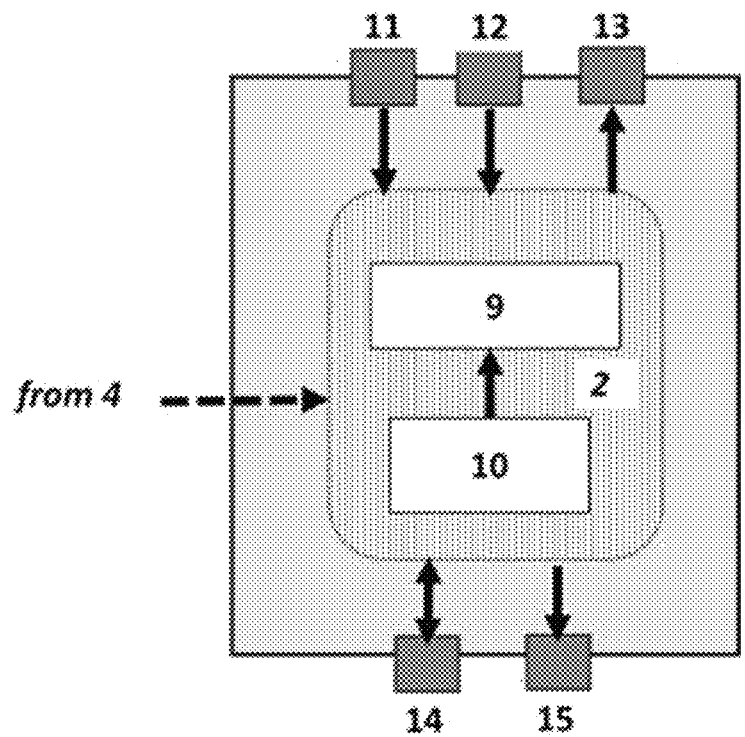
FIG. 4. Diagram of the signal processing module forming part of the accessory of the present invention, wherein the reference numbers indicated therein are defined as: (2) signal processing module, (4) power supply, (9) computer, (10) video converter, (11) keyboard input, (12) mouse input, (13) monitor output, (14) video input and output, (15) data output.

The present invention is directed to an endoscope attachment accessory with telemetric function, which corresponds to a biomedical device that assists surgical and endoscopic procedures to increase accuracy. Said accessory mainly consists of, and not limited to, three main modules (as generally illustrated in FIG. 1): an alignment module (1) (shown in FIG. 2), a laser module (3) (FIG. 3) and a signal processing module (2) (FIG. 4), which are powered by the same power source (4), preferably alternating current (AC). In particular, the three modules (1, 2, 3) of the accessory of the invention are housed and integrated in a housing (as illustrated in FIG. 1) and are attached to an optical fiber, an endoscope, and a monitor, all of which are external to the housing.

In this same aspect of the invention, the alignment module (1) comprises an electronic control board (6), one or more sensors, one or more cameras, a touch screen (19), one or more power sources (4), and a series of mechanical and electronic elements described below, which compose an electromechanical system that aligns the laser fiber with the tip of the endoscope so that the tip of the laser optical fiber, the center of the working channel of the endoscope and the center of the distal tip of the endoscope are joined together in a straight line (this alignment is indispensable for the correct operation of the telemeter based on the triangulation principle).

Thus, the alignment module (1) comprises a coiler (7) in charge of moving the tape coiler that holds the fiber around the endoscope tip, where said coiler (7) includes a gear and electronic control mechanism (23), to ensure a homogeneous and sufficient clamping area to avoid misalignment of the laser optical fiber; an alignment press (22) and clamping means, to prevent misalignment of the laser fiber during coiling; a cutting mechanism (21), which cuts the tape after coiling is complete; a clamping means coiler (20), which coils the tape to hold the fiber optic tip around the endoscope tip; a clamping media meter, which determines when the predetermined clamping length with warning system (24) has been reached, and optional a battery backup. All elements of the coiler (7), as well as the camera and sensor (27), and the power supply (4), are connected to the electronic control board (6), which supports the circuit, wherein the electronic control board (6) is connected to a processor (9), and receives control commands from the alignment module (1).

Specifically, the alignment module (1) includes two parallel holes (25, 26) through which the tip of the endoscope and the tip of the optical fiber enter until they reach a stop. This stop aligns the two tips on an axis. Inside the alignment module (1), the sensor and camera (27) transmit data to the processor or computer (9) of the processing module (2). The camera, sensor and stop ensure that the working channel of the endoscope and the optical fiber are aligned. Otherwise, the operator must rotate the endoscope tip until it reaches the proper position. The alignment press (22) fixes the endoscope tip and the fiber momentarily in the proper position, while the coiling of the tape that allows the fiber to be clamped to the endoscope tip is carried out, as previously described.

The gear and electronic control mechanism (23) cause the coiler (7) to rotate around the tip of the aligned endoscope and fiber optic. The coiler wraps the clamping means around the endoscope and fiber optic, which allows them to be permanently clamped. Once the clamping means have completed their predetermined path around the tips of both elements, the clamping means meter with alert system (24) emits a notification, which may be audible or written via the video input and output (14).

Finally, the cutting mechanism (21) cuts the clamping means and the endoscope, which already has the optical fiber clamped at its tip, is removed. The alignment of the fiber with the center of the working channel and the center of the endoscope tip is fundamental to obtain valid measurements based on the triangulation principle, as this configures a cathetus (side of a triangle) with a fixed distance that allows the other cathetus (corresponding to the distance between the endoscope tip and the object on which the laser spot is projected) to be determined based on the angle of the hypotenuse.

In the same aspect, the alignment module (1) has a touch screen (19) that allows the alignment process of the fiber with the center of the working channel and the center of the endoscope tip to be performed interactively.

In one aspect of the invention, the laser control module (3) comprises a laser generator (17), an external optical fiber with collimator, electronic control means (16) for adjusting the laser intensity and an external optical fiber connector (18). In particular, this assembly generates a beam of light that is reflected on the internal surfaces of the body of interest. From this reflection, the distance is determined, the equipment is calibrated together with the signal processing module (2), making use of the signal processing module (2) and in real time.

More particularly, the laser generator (17) is attached to the external optical fiber. This fiber has a collimator at one end (element that allows concentrating the light beam on a single point), which is aligned with the working channel of the endoscope, for which the alignment module (1) is provided. The opposite end of the optical fiber has a connector, which is attached with the external connector (18) of the laser control module (3) once the alignment process is completed. During the procedure, the tip of the endoscope and the tip of the optical fiber with collimator that have been clamped by the alignment module (1) using the mechanism described above, enter the body orifice. The laser generator (17) produces a beam which travels through the optical fiber to the collimator, through which it is projected. The electronic control means (16) adjusts the intensity of the laser, and the laser control module (3) adjusts and controls the generation of the light beam that allows triangulation and obtaining position and distance data.

In the same aspect of the invention, the signal processing module (2), comprising the computer (9), which houses logic means, is connected to a video converter (10). The processing module (2) also includes a video input and output (14), keyboard and mouse connectivity (11,12), an additional monitor output (13), and a data output (15).

Figure 5:
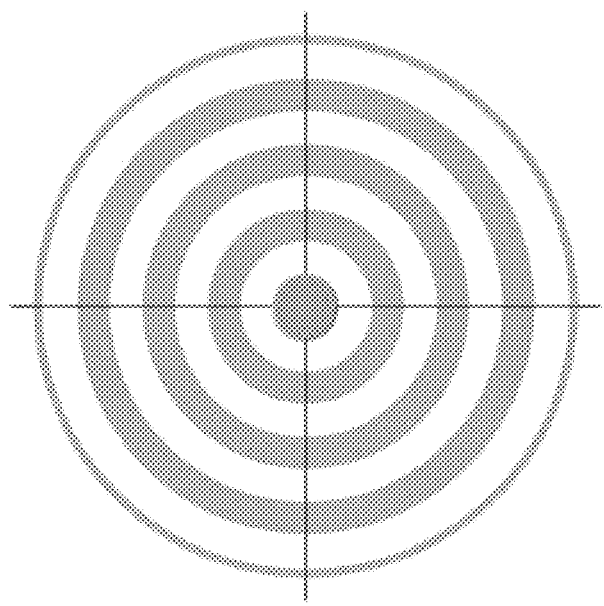
FIG. 5. Digital laser triangulation polar grid.

In the particular aspect, the computer (9) includes a processor, a software or computer program that stores and processes the information sent by the video and a storage memory. The memory allows storing the information of the procedure together with the area and distance measurement data obtained. The processor is responsible for controlling the elements of the various modules and perform image processing. The computer logic means (9) executes the instructions stored by means of a computer program in the computer readable medium to calculate distances and areas and thus generate a polar grid (as illustrated in FIG. 5) of triangulation with circles that serve to identify the distance between the tip of the endoscope and the object on which the laser spot is projected (FIG. 5), where the polar grid is displayed on the monitor of the endoscope by means of the video input and output (14).

In this way the software of the device allows to calculate the radius between the center of the field of view and the center of the laser spot, this software establishes a correlation through a regression equation between this radius and the distance between the tip of the endoscope and the object on which the laser spot is projected. During telemeter measurements, the regression equation obtained previously during calibration is used to plot the polar grid circles at particularly representative distances and to make an exact quantitative determination of the distance between the endoscope tip and the object on which the laser spot is projected.

The video input and output (14) are the port through which the image data captured by the endoscope camera is acquired and processed in the endoscope image processor. The logic means perform image pre-treatment, filtering, and processing in order to improve the quality of the image. Once a high-quality image is obtained, the two-dimensional and three-dimensional analysis of the images and/or videos coming from the endoscope camera is carried out by means of the triangulation principle. This process makes the determination of distances and areas.

In particular, the additional monitor output (13) allows to connect a monitor other than the endoscope system monitor, in order to program the computer (9). The data output (15) allows to generate a copy of the information stored in the memory of the computer (9).

In the same particular aspect, the determination of distances and areas is performed by means of the laser light beam and the digital polar grid, where the light beam is projected at different positions within the polar grid. By means of the processing equation and the relative position of the light beam, the corresponding calculations are made.

In particular, the signal processing module (2) comprises a video converter (10), which allows the conversion of the digital or analog image signal coming from the endoscope.

The alignment module (1), the laser control module (3), and the signal processing module (2) are interconnected as follows: the alignment module (1) is connected to the processing module (2) via the electronic board (6), which is connected to the processor (9); the laser control module (3) is connected to the processing module (2) via the laser control electronics means (16), which are connected to the processor (9).

In another aspect of the invention, the system has a battery backup in case of power failure.

In a preferred embodiment of the present invention, the clamping means of the alignment module (1) is a Teflon tape or any adhesive tape wherein this alignment module (1) can clamp the optical fiber and the distal end of the endoscope (endoscope tip) in horizontal, vertical or other angles of the Cartesian plane. The clamping can be done using a horizontal platform on which the endoscope tip and the fiber optic tip rest or on a vertical platform on which the endoscope tip and the fiber optic tip are inserted or on platforms at other angles of the Cartesian plane that clamp the endoscope tip and the fiber optic tip.

Such clamping platforms may be movable, with the ability to be removed once coiling of the tape securing the optical fiber to the endoscope tip progresses; or they may be fixed by holding the tips of the endoscope and the optical fiber at a small distance that does not interfere with the coiling of the tape. The clamping can be done by wrapping a tape around the endoscope and fiber optic tips or by using an expanded elastic tube with the aid of arms or a pneumatic negative pressure clamping system; where the endoscope and fiber optic tips are inserted and aligned within the expanded elastic tube and then the elastic tube is released so that when it returns to its original size it clamps the endoscope and fiber optic tips.

In the same aspect, video input and output connectivity (14), keyboard and mouse connectivity (11,12), and additional monitor output (13), and data output (15), are ports, preferably of USB type, belonging to the computer (9), on the signal processing module (2). The computer (9) is attached to the image processor of the endoscope and includes a processor and a computer program that stores instructions executed by the processor to calculate the distance between the tip of the endoscope and the object on which the laser spot is projected.

In this same preferred aspect, the image pre-processing performed by the logic means of the signal processing module (2) constructs a digital image based on electrical signals generated by the image processor of the endoscope. The processor eliminates the barrel distortion of the camera and improves the image quality. After pre-processing, the image is filtered, segmented and analyzed in a Cartesian coordinate plane. The laser spot projected within the digital image is identified, the center of the field of view, the center of the laser spot, the radius between the center of the laser spot and the center of the field of view are determined and according to the regression equation obtained during the telemeter calibration, based on the triangulation principle, the distance between the endoscope tip and the object on which the laser spot is projected is determined. The areas and volumes of the objects on which the laser spot is projected are also determined by equations based on the distance between the imaging lens at the tip of the endoscope and the object to be measured and the refraction of the imaging lens.

In the same preferred aspect, the laser generator (16) of the laser control module (3) emits a beam of red (670 nm) or green (532 nm) light or another color of the spectrum visible to the human eye.

The terms "comprising" or "including" used throughout the present document are meant to be extensive and non-limiting, i.e., the present invention may comprise other additional components or features, which are not specifically defined within the present description, but which are obviously used for the respective operation of the device or system, and are clear to a person skilled in the art.

Although the foregoing description defines the preferred embodiments of the present invention, it also contemplates within the scope of the present document the various modifications that may be apparent to a person skilled in the art, wherein said scope is in no way limited to the preferred embodiments, but is defined solely by the appended claims and the subject matter therein.

In the following, a series of examples will be defined which enable the superiority of the present device or accessory to be evidenced by means of a real application, where such examples are given in a general way and are not intended to define or limit the invention to the embodiments or particulars defined therein, such as may be clear to a person skilled in the art.

EXAMPLES

Determination of Nodular Lesion Area in Larynx

The device was attached to an endoscope and entered through the patient's nose. The light beam was projected on the surface of the larynx, images were obtained and processed by the logical means, and using the scope, the area of the nodular lesion located in the right vocal cord was determined. In a later procedure, using the same approach, a 20% growth of the lesion was evidenced.

Determination of Membranous Stenosis Area in Trachea

The device attached to an endoscope was used, entered through the patient's nose and the light beam was projected onto the surface of the trachea. Images were obtained and processed by logical means, and a scar was observed in the middle third of the trachea producing a membranous stenosis of the airway. The diameter of the airway before and after stenosis was 16 mm and at the site of stenosis it was 3 mm, which corresponds to a stenosis of 81.3%. The length of the lesion was 5 mm, which was determined by using the device, the polar grid, and logical means. With these measurements, it was determined that the stenosis required interventional treatment with endoscopic electrosurgery, dilatation, and implantation of a silicone stent 16 mm in diameter and 3 cm in length.

Tracheal Diameter Determination

The device attached to an endoscope was used, entered through the patient's nose, and the light beam was projected on the surface of the trachea, images were obtained and processed by the logical means. Through this processing and the use of the polar grid, it was possible to measure the diameter of the patient's trachea, which was 14 mm. With this measurement, it was determined that the external diameter of the rigid endoscope to be used for the patient's bronchoscopy was 12 mm, since a diameter greater than or equal to 14 mm could lacerate the tracheal mucosa.

Determination of Main Bronchus Diameter

The device was attached to an endoscope, entered through the patient's nose, the light beam was projected onto the surface of the left main bronchus, and images were obtained. By processing the images by logical means, a dynamic collapse of the left main bronchus was observed. The measurements made by the device, the scope and the logic processing showed an inspiratory diameter of the left main bronchus of 12 mm and an expiratory diameter of 1 mm, for a dynamic airway obstruction of 92%, which warrants interventional treatment with a 12 mm external diameter silicone bronchial stent (corresponding to the diameter of the left main bronchus).

The invention claimed is:

1. An endoscope attachment accessory with telemetry function comprising;
    a laser control module (3),
    an alignment module (1) and
    a signal processing module (2),
    wherein the endoscope attachment accessory is attached to an external endoscopic system comprising an optical fiber, an endoscope and a monitor,
    wherein the laser control module (3) comprises:
        a laser generator (17),
        an optical fiber connector (18) attached to the optical fiber of the external endoscopic system, and
        is configured to adjust a laser intensity of the laser generator and adjust and control generation of a laser light beam that allows triangulation and obtainment of position and distance data,
    wherein the alignment module (1) comprises:
        one or more cameras and one or more sensors (27),
        a coiler (7) configured to hold the optical fiber around a tip of the endoscope which ensures clamping of the optical fiber and the endoscope tip and avoid misalignment of the optical fiber during coiling,
        an electronic aligner control board (6),
    wherein the signal processing module (2) comprises:
        a computer (9) configured to calculate distances and areas and thus generate a polar grid of triangulation with circles that serve to identify a distance between the tip of the endoscope and an object on which a laser spot is projected, where the polar grid is displayed on the monitor of the endoscopic system by means of a video input and output (14),
        a video converter (10) configured to convert digital or analog image signal coming from the endoscope,
    wherein the alignment module (1) is connected to the signal processing module (2) via the electronic board (6) which in turn is connected to the processor (9) of the signal processing module, the laser control module (3) is connected to the signal processing module (2) which in turn is connected to the processor (9) of the signal processing module.

2. The endoscope attachment accessory with telemetric function according to claim 1, wherein the laser control module (3), the alignment module (1) and the signal processing module (2) are housed in a housing.

3. The endoscope attachment accessory with telemetric function according to claim 1, wherein the coiler further comprises an alignment press (22) configured to prevent misalignment of the optical fiber during coiling.

4. The endoscope attachment accessory with telemetric function according to claim 1, wherein in the alignment module (1), the one or more cameras and one or more sensors (27) transmits position and distance data to the computer (9) of the processing module (2).

5. The endoscope attachment accessory with telemetric function according to claim 1, wherein the laser control module (3) generates a beam of light that is reflected on internal surfaces of a body of interest, such that from the reflection of the beam of light a distance is determined and together with the signal processing module (2) the distance is calibrated in real time.

* * * * *